(12) United States Patent
Warburton-Pitt et al.

(10) Patent No.: US 6,290,265 B1
(45) Date of Patent: *Sep. 18, 2001

(54) TUBING AND CONNECTOR ASSEMBLY AND METHOD AND MOLDING

(75) Inventors: Stephen Ronald Warburton-Pitt, Queensbury, NY (US); Rick Alan Steele, Newton, NJ (US)

(73) Assignee: Saint-Gobain Performance Plastics Corporation, Worchester, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,450

(22) Filed: Aug. 11, 1997

(51) Int. Cl.$^7$ .................................................. F16L 47/02
(52) U.S. Cl. .................. 285/131.1; 285/423; 285/293.1; 285/285.1; 604/284
(58) Field of Search ................... 285/FOR 138, 285/133.11, 285.1, 293.1, 131.1, 423; 604/284; 128/214 R

(56) References Cited

U.S. PATENT DOCUMENTS

| | | | |
|---|---|---|---|
| 3,463,691 | * | 8/1969 | Martin .............................. 285/294.1 |
| 3,540,223 | * | 11/1970 | Ebbe .............................. 285/133.11 |
| 4,070,044 | * | 1/1978 | Carrow .......................... 285/133.11 |
| 4,076,282 | * | 2/1978 | Scott, Jr. et al. ................. 285/285.1 |
| 4,203,436 | * | 5/1980 | Grimsrud ......................... 128/214 R |
| 4,596,557 | * | 6/1986 | Pexa ...................................... 604/284 |
| 4,661,110 | * | 4/1987 | Fortier et al. ........................ 604/284 |
| 4,815,769 | * | 3/1989 | Hopperdietzel ................... 285/131.1 |
| 4,997,213 | * | 3/1991 | Traner et al. ..................... 285/131.1 |
| 5,254,097 | * | 10/1993 | Schock et al. ...................... 604/284 |
| 5,292,305 | * | 3/1994 | Boudewijn et al. ................ 604/283 |
| 5,411,300 | * | 5/1995 | Mitsui ............................. 285/133.11 |
| 5,429,397 | * | 7/1995 | Kanao .............................. 285/293.1 |
| 5,447,341 | * | 9/1995 | Hartel et al. ...................... 285/285.1 |
| 5,453,088 | * | 9/1995 | Boudewijn et al. .................. 604/43 |
| 5,568,949 | * | 10/1996 | Andre ............................... 285/285.1 |

FOREIGN PATENT DOCUMENTS

| | | | |
|---|---|---|---|
| 580160 | * | 7/1959 | (CA) ................................... 285/179 |
| 40-6042687 | * | 2/1994 | (JP) ............................. 285/FOR 138 |
| 40-6101791 | * | 4/1994 | (JP) ............................. 285/FOR 138 |
| 40-6101792 | * | 4/1994 | (JP) ............................. 285/FOR 138 |

* cited by examiner

Primary Examiner—Eric K. Nicholson
(74) Attorney, Agent, or Firm—Wood, Herron & Evans L.L.P.

(57) ABSTRACT

A connector and tubing assembly including a multi-lumen molded connector having at least three flexible tubes also molded into the connector. The connector may be "Y" shaped and include three flexible tubes. A process of making the connector and tubing assembly involves forming a first part of the connector with two tubes molded therein and then removing an internal mold member prior to molding the final connector portion and third tube in place.

8 Claims, 3 Drawing Sheets

TUBING AND CONNECTOR ASSEMBLY AND METHOD AND MOLDING

FIELD OF THE INVENTION

The present invention generally relates to tubing and connector assemblies and, specifically, to those assemblies utilizing multi-lumen connectors.

BACKGROUND OF THE INVENTION

Tubing assemblies including flexible tubing and multi-lumen connectors have been used in many applications, including those that require a high degree of assurance that contamination will not enter the system by way of the connector. Applications of such systems include closed systems in the medical field in which the flexible tubing may be clipped into a peristaltic pump used for medical purposes. Past tubing and connector assemblies have required various means for securing the connectors to the flexible tubing, including mechanical connectors or adhesive. These systems are therefore susceptible to contaminants entering the system at the point of connection.

Connectors have been molded directly to two tubes, however, to Applicant's knowledge, there has never been an acceptable method of directly molding a multi-lumen connector to three or more flexible tubes. In general, this is due to the problems associated with maintaining fluid passages within the connector and between the multiple tubes during and after the molding process.

Therefore, it would be desirable to provide a tubing and connector assembly as well as a method of molding such an assembly in a cost-efficient manner to produce an integral tubing and connector assembly that maintains a high degree of system integrity.

SUMMARY OF THE INVENTION

The present invention therefore generally provides an integral connector and tubing assembly including a one-piece, multi-lumen connector having at least three connector portions and at least three tubes. Each of the tubes is molded into one connector portion, and a fluid path extends within each connector portion and communicates between each of the three tubes. The connector may be "Y" shaped with three connector portions respectively receiving three flexible tubes. The connector assembly may also have additional connector portions and a like number of additional flexible tubes. The connector is preferably molded from liquid silicone while the tubes are preferably flexible and formed from a thermoset silicone.

A method of molding a connector and tubing assembly of the present invention generally includes molding first and second portions of a connector around respective ends of first and second tubes while maintaining fluid passages through the first and second portions and in communication with internal fluid bores of the first and third tubes and then molding a second portion of the connector around an end of a third tube and connected with the first and second portions while maintaining a fluid passage between the end of the third tube and the fluid passages in the first and second portions. Preferably, first and second rod members are placed in the respective ends of the first and second tubes prior to molding the first and second portions and a third rod member is placed in the end of the third tube prior to molding the third portion. Prior to molding the third portion, the first and second rod members are removed from the first and second portions of the connector. The first and second rod members may be part of a "Y" shaped member and each molding step may be performed in a single mold.

A more specific and preferred method of making the connector and tubing assembly according to this invention includes the steps of: connecting the internal fluid bores of respective ends of first and second tubes to first and second rod members; placing the rod members and the ends of the first and second tubes into a first mold cavity; filling the first mold cavity with curable material to form a first and second connector portions around the ends of the first and second tubes and the first and second rod members such that the first and second rod members form fluid passages through the connector; withdrawing the first and second rod members; inserting a third rod member into the internal fluid bore in an end of a third tube; placing the end of the third tube into a second mold cavity and in engagement with at least one of the fluid passages; filling the second mold cavity with additional curable material to form a third connector portion; and removing the third rod member.

Preferably, the first and second mold cavities communicate with one another in the same mold. The mold may be an injection mold. For allowing the use of a single mold, a mold insert may be placed within the second mold cavity prior to filling the first mold cavity with the curable material. This prevents the curable material from filling the second mold cavity during this initial molding step. The mold insert is generally solid but preferably includes a central hole. The first and second rod members may be part of a "Y" shaped member. In this case, the second step further includes placing a third leg of the "Y" shaped member within the central hole of the insert and placing the insert within the second mold cavity. The mold insert may have a protrusion surrounding the hole and this protrusion may then form a recess in communication with the passages in the initially formed connector portions. This recess can be used to locate or receive the third tube prior to the second molding step, i.e., prior to filling the second mold cavity with additional curable material.

Various objects and advantages of the invention will become more readily apparent to those of ordinary skill upon review of the following detailed description of one preferred embodiment taken in conjunction with the accompanying drawings.

DETAILED DESCRIPTION OF THE PREFERRED EMBODIMENT

Figure 1:
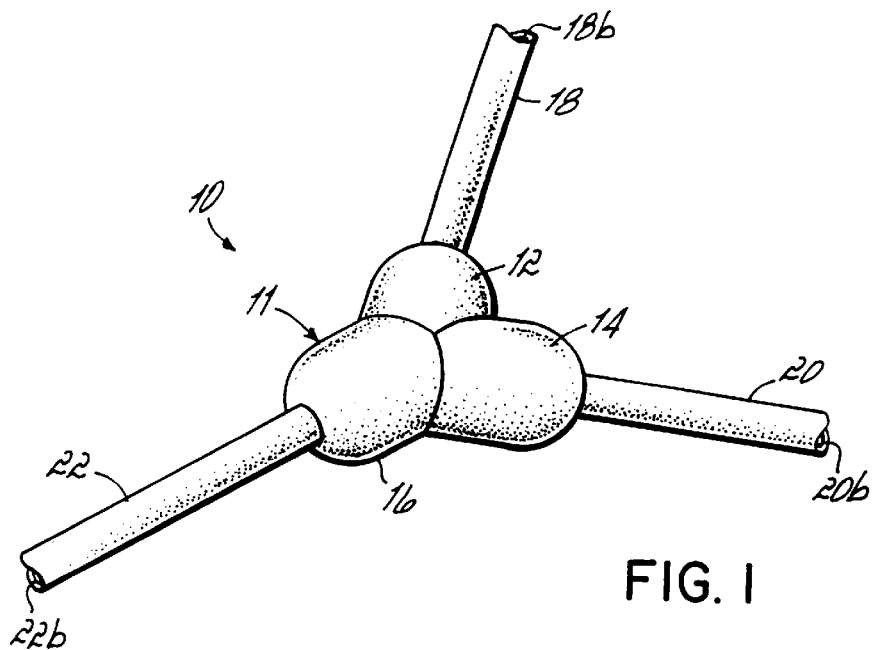
FIG. 1 is a perspective view of a connector and tubing assembly constructed in accordance with the preferred embodiment of this invention.

FIG. 1 illustrates a connector and tubing assembly 10 after a connector 11 has been molded with portions 12, 14, 16 holding flexible tubes 18, 20, 22 together for fluid communication therebetween. This structure therefore forms an integral fluid conveyance system which is not easily compromised at the junctions between connector 11 and tubes 18, 20, 22.

FIGS. 2–6 illustrate the preferred manner of making the connector and tubing assembly 10. First, a mold half 30 is provided having an internal mold cavity 31 in the shape of the desired connector 11. Cavity 31 is preferably formed by three smaller cavities 32, 34, 36 each having respective ports 38, 40, 42. Curable mold material, such as conventional liquid silicone, may be injected through ports 38, 40, 42 into cavity 31 after a second mold half is brought into facing engagement, as will be described below. Recesses 44, 46, 48 are respectively provided for holding tubes 18, 20, 22 such that respective connecting ends 18a, 20a, 22a extend within cavity portions 32, 34, 36. An inner mold member 50 is provided and may be formed from low density polyethylene (LDPE). Mold member 50 may be generally "Y" shaped and serves to help form a fluid passageway between the internal fluid bores 18b, 20b, 22b of tubes 18, 20, 22 after molding is complete.

Figure 2:
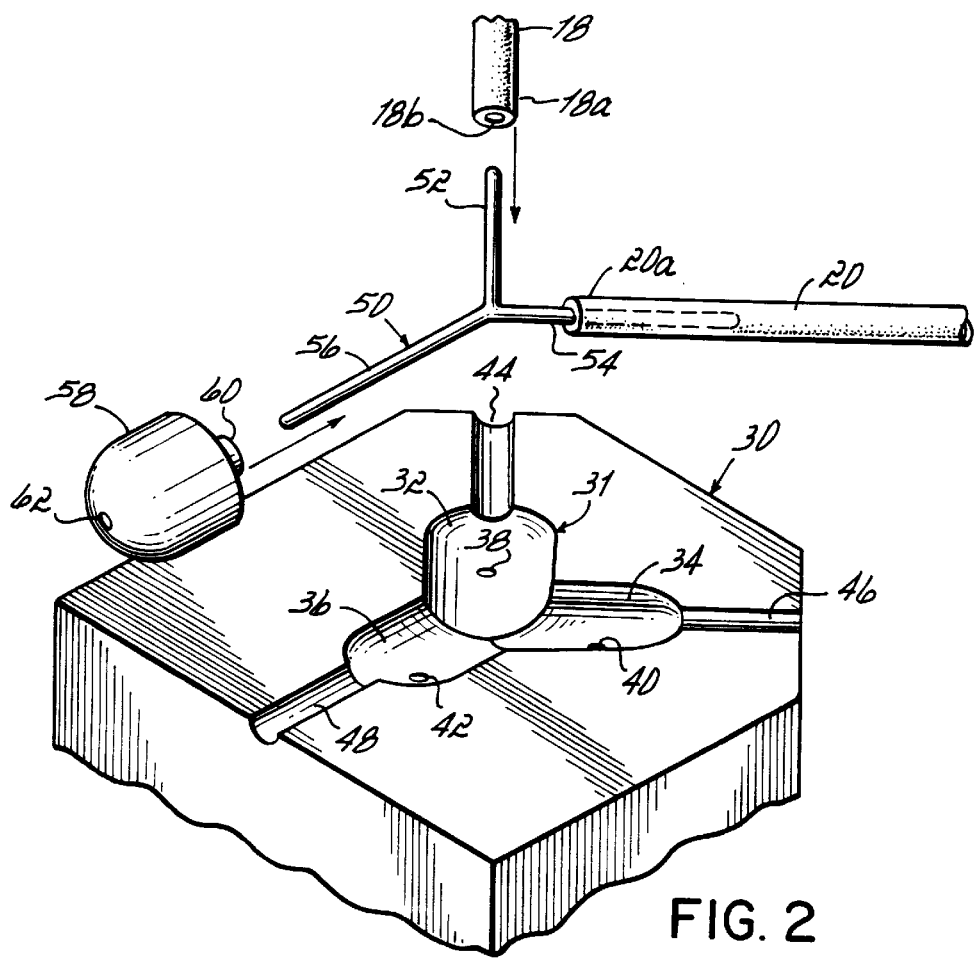
FIG. 2 is a perspective view, partially exploded, of the initial steps of a molding process used to form the product of FIG. 1.

Referring to FIG. 2, first and second tubes 18, 20 are inserted onto respective first and second rod members 52, 54 of mold member 50 and a third rod member or leg 56 receives a mold insert 58 which may be formed of metal, such as stainless steel, and generally takes the shape of cavity portion 36. Mold insert 58 includes a central protrusion on an end facing cavity portions 32, 34 and includes a central hole 62 for receiving rod member 56 of inner mold member 50.

Figure 3:
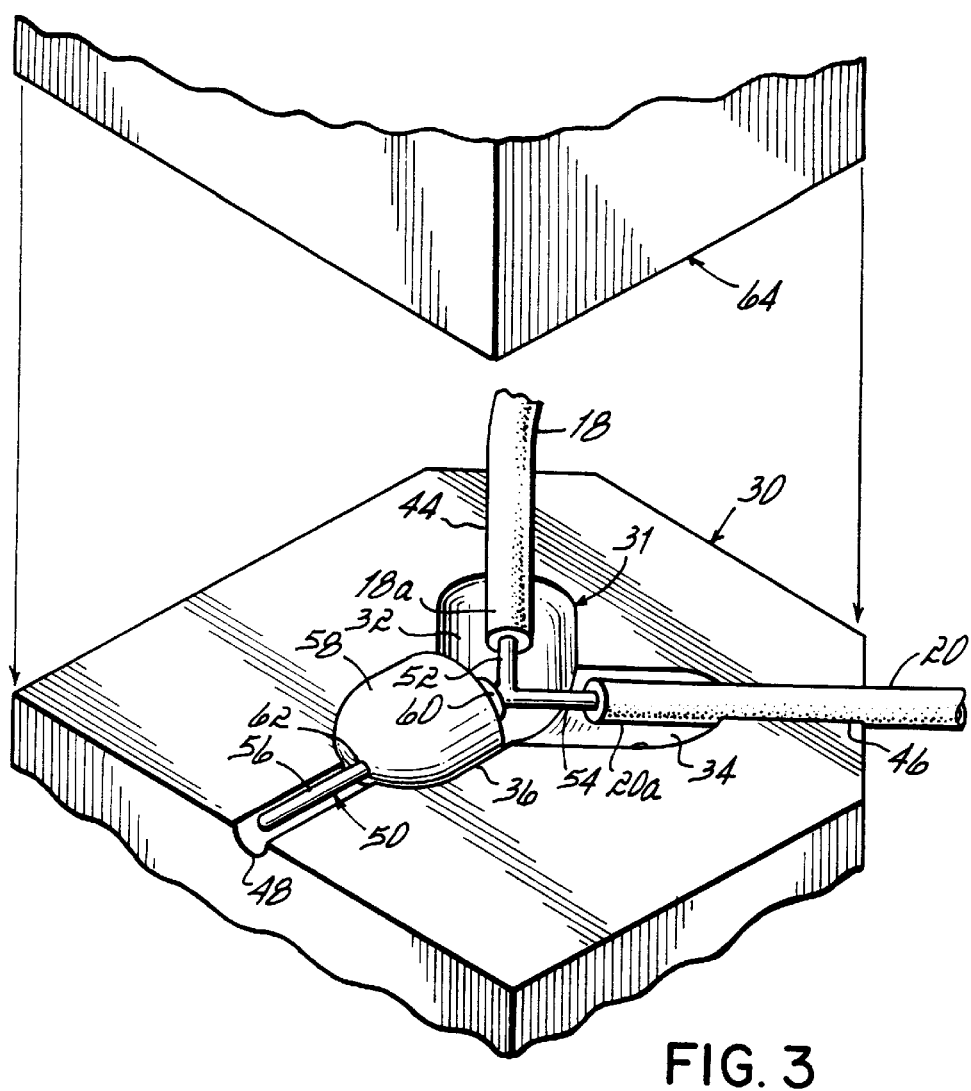
FIG. 3 is a perspective view of the molding process at a later stage.
Figure 4:
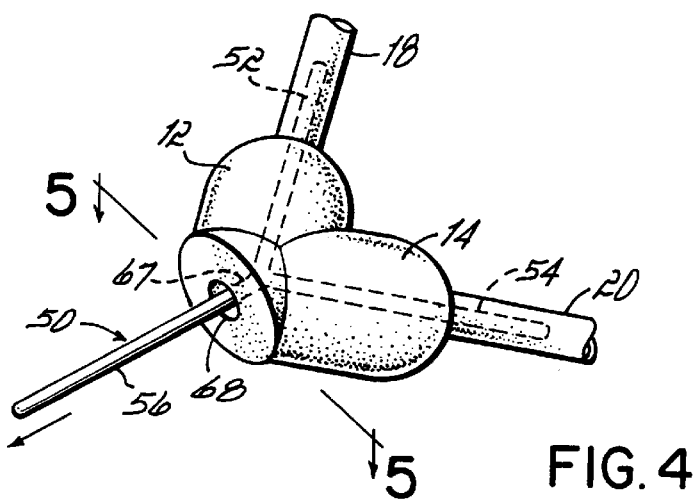
FIG. 4 is a perspective view of an intermediate product formed by the molding process.

The items described with respect to FIG. 2 are attached together and placed within mold half 30 as shown in FIG. 3 and a second mold half 64 is brought into facing engagement with mold half 30. It will be understood that mold half 64 has cavities and recesses (not shown) which are the mirror image of cavity portions 32, 34, 36 and recesses 44, 46, 48 of mold half 30. The mold is then shot, i.e., curable mold material is injected into cavities 32, 34 of mold 30 through ports 38, 40, and after curing thereof, an intermediate product as shown in FIG. 4 will result. In this step, cavities 32, 34 act as one cavity for producing connector portions 12, 14 which, in turn, form a single integral connector portion. Metal mold insert 58 is removed from rod member 56 and then the "Y" shaped inner mold member 50 is withdrawn from connector portions 1 2, 14 and tubes 18, 20 by pulling on rod member 56. Mold member 50 is flexible and may be withdrawn with reasonable manual force being applied by a pair of pliers.

Figure 5:
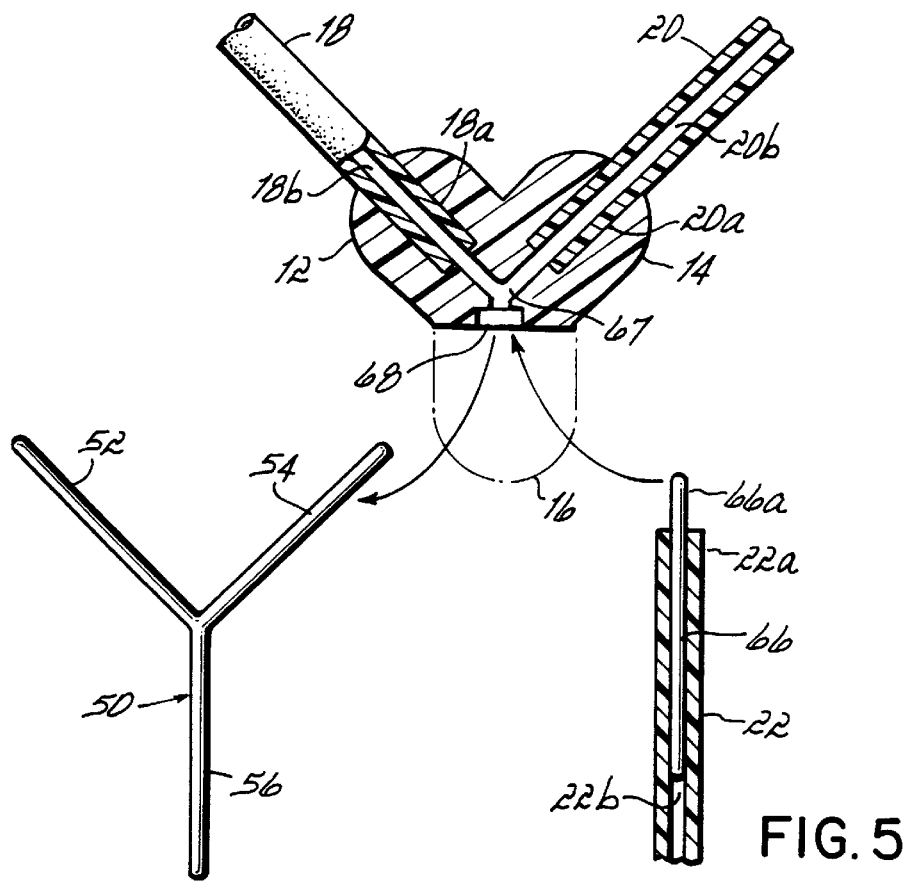
FIG. 5 is a sectional view taken generally along line 5—5 of FIG. 4 and also showing the removal of an internal "Y" shaped mold member as well as an additional tube containing a rod used later in the molding process; and, FIG. 6 is the intermediate product shown in perspective within the mold cavity with the third tube in place just prior to the final molding step.
Figure 6:
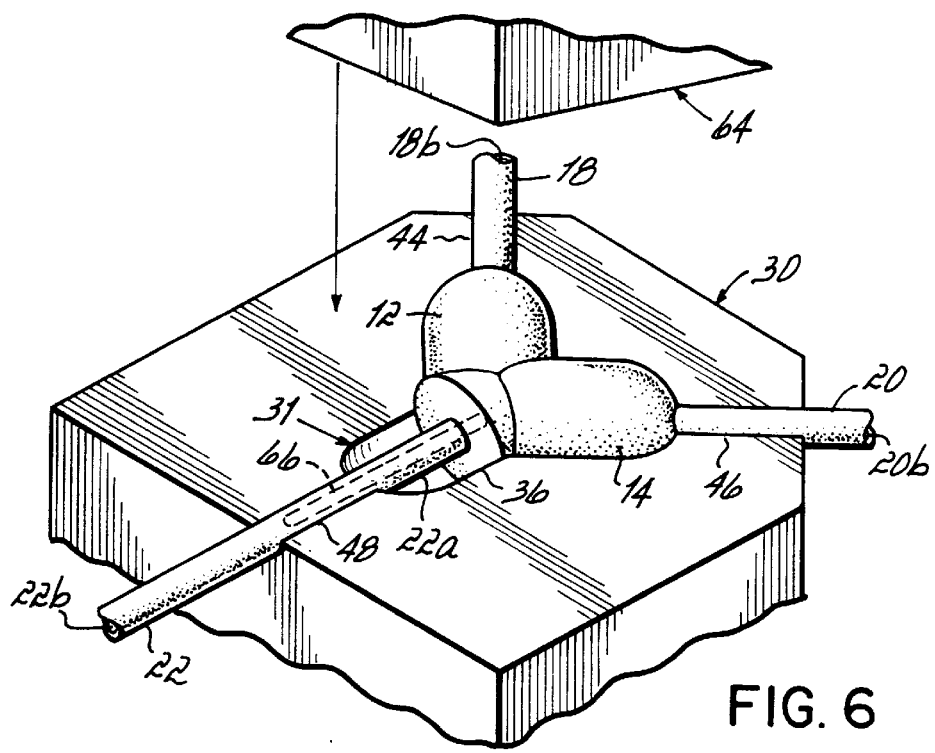

After mold member 50 is withdrawn, as shown in FIG. 5, the third tube 22 is prepared for the final molding step. That is, a straight plastic rod 66, also preferably formed of LDPE, is inserted into tube end 22a with a small portion 66a extending outwardly from end 22a. This assembly is placed into mold half 30 as shown in FIG. 6 with rod end 66a extending into a passage 67 formed within connector portions 12, 14 by rod member 56 and with tube end 22a held within a recess 68 formed by protrusion 60 (FIG. 2) on mold insert 58. It will therefore be appreciated that rod end 66a will maintain fluid passage 67 open during the second molding step. Mold half 64 is again brought into facing engagement with mold half 30 and the final cavity 36 is injected with curable mold material, again taking the form of conventional liquid silicone. After this portion of connector 11 has cured, rod 66 may be blown out of tube 22 by injecting pressurized air into tube 18 after tube 20 has been plugged, or into tube 20 after tube 18 has been plugged.

Although a preferred embodiment of the present invention has been shown and described, along with a preferred method of making the product of this invention, the details provided herein are not intended to limit the scope of protection. For example, certain modifications such as the incorporation of additional connector portions and tubes are possible as well as the use of any number of shapes for the connector. The connector portions do not have to have readily distinguishable shapes as specifically preferred herein, but may be formed as part of one shape. It will also be appreciated that multiple connectors of this invention may be used in a single system. Those of ordinary skill will readily recognize many further modifications within the spirit and scope of the inventive concepts. Therefore, Applicants intend to be bound only by the legal scope of the appended claims.

What is claimed is:

1. An integral connector and tubing assembly for transporting health care fluids, the assembly comprising:
   a) a one piece multi-lumen connector formed from a resilient material and having at least three connector portions;
   b) at least three flexible tubes, each of said tubes being formed from the same resilient material as said connector and molded into one connector portion; and
   c) a fluid path defined by an interior passage molded into said one-piece multi-lumen connector and extending within each connector portion to communicate between each of the three tubes.

2. The connector and tubing assembly of claim 1 wherein the connector is molded into a "Y" shape.

3. The connector and tubing assembly of claim 1 wherein the connector is formed from a liquid silicone.

4. The connector and tubing assembly of claim 1 wherein the tubes are formed from a thermoset silicone.

5. An integral connector and tubing assembly for transporting health care fluids, the assembly comprising:
   a) at least three flexible tubes formed from a resilient material, each tube having an exterior surface, a connecting end and an internal fluid bore extending inwardly from the connecting end;
   b) a one-piece connector body formed from the same resilient material as said flexible tubes having at least three connector portions and a central portion, each connector portion having a tube-receiving port molded around the connecting end of a different one of said tubes to establish a fluid-tight seal between each said connector portion and the exterior surface of its respective connecting end; and
   c) a fluid path defined by an interior passage molded into said central portion and communicating with the internal fluid bores of each of said tubes proximate their respective connecting ends.

6. The assembly of claim 5 wherein the connector body is molded silicone and the tubes are thermoset silicone.

7. An integral connector and tubing assembly for transporting health care fluids, the assembly comprising:
   a) a one piece multi-lumen connector formed from a material and having at least three connector portions;
   b) at least three flexible tubes, each of said flexible tubes being formed from the same material as said connector, each flexible tube being molded into one connector portion; and
   c) a fluid path defined by an interior passage molded into said one-piece multi-lumen connector and extending within each connector portion to communicate between each of the three tubes.

8. An integral connector and tubing assembly for transporting health care fluids, the assembly comprising:
   a) a one piece multi-lumen connector formed from a material and having at least three connector portions;
   b) at least three flexible tubes, each of :said flexible tubes being formed from same material as said connector and molded into one connector portion; and
   c) a fluid path defined by an interior passage molded into said one-piece multi-lumen connector and extending within each connector portion to communicate between each of the three tubes, said interior passage defined by smooth bores within said connector and smoothly transitioning to bores in each of said flexible tubes.

* * * * *

(12) EX PARTE REEXAMINATION CERTIFICATE (5728th)
United States Patent
Warburton-Pitt et al.

(10) Number: US 6,290,265 C1
(45) Certificate Issued: Mar. 27, 2007

(54) TUBING AND CONNECTOR ASSEMBLY AND METHOD AND MOLDING

(75) Inventors: Stephen Ronald Warburton-Pitt, Queensbury, NY (US); Rick Alan Steele, Newton, NJ (US)

(73) Assignee: Saint-Gobain Performance Plastics Corporation, Worcester, MA (US)

Reexamination Request:
No. 90/006,855, Nov. 12, 2003

Reexamination Certificate for:
Patent No.: 6,290,265
Issued: Sep. 18, 2001
Appl. No.: 08/909,450
Filed: Aug. 11, 1997

(51) Int. Cl.
*F16L 41/00* (2006.01)

(52) U.S. Cl. ............... 285/131.1; 285/423; 285/293.1; 285/285.1; 604/284

(58) Field of Classification Search ............... None
See application file for complete search history.

(56) References Cited
PUBLICATIONS

Sani–Tech Product Catalog, 1991, pp. 1–10.

*Primary Examiner*—David Bochna

(57) ABSTRACT

A connector and tubing assembly including a multi-lumen molded connector having at least three flexible tubes also molded into the connector. The connector may be "Y" shaped and include three flexible tubes. A process of making the connector and tubing assembly involves forming a first part of the connector with two tubes molded therein and then removing an internal mold member prior to molding the final connector portion and third tube in place.

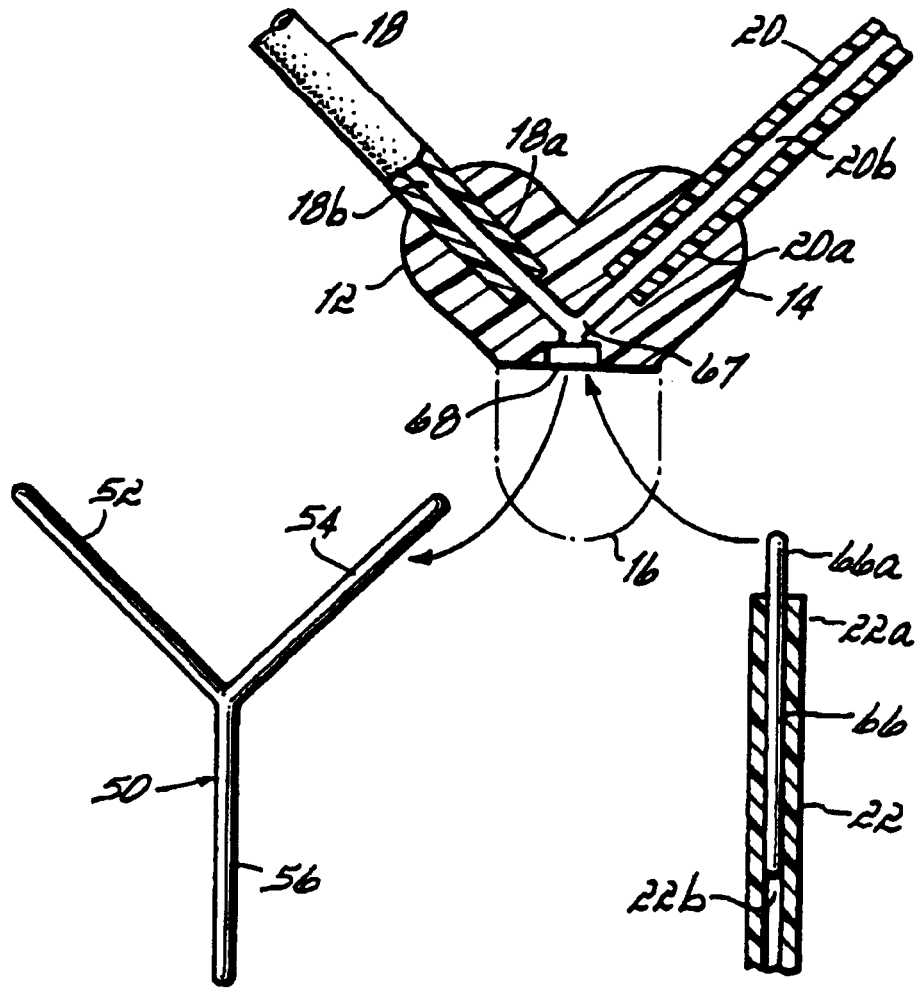

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *